(12) United States Patent
Nishihara et al.

(10) Patent No.: US 11,573,414 B2
(45) Date of Patent: Feb. 7, 2023

(54) ENDOSCOPE SYSTEM, PROCESSOR, AND ENDOSCOPE

(71) Applicant: OLYMPUS CORPORATION, Hachioji (JP)

(72) Inventors: Rintaro Nishihara, Tokyo (JP); Sho Nakamura, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 494 days.

(21) Appl. No.: 16/693,217

(22) Filed: Nov. 22, 2019

(65) Prior Publication Data
US 2020/0174245 A1 Jun. 4, 2020

(30) Foreign Application Priority Data

Dec. 4, 2018 (JP) .............................. JP2018-227499

(51) Int. Cl.
*A61B 1/00* (2006.01)
*G02B 23/24* (2006.01)
(Continued)

(52) U.S. Cl.
CPC ........ *G02B 23/2438* (2013.01); *A61B 1/0002* (2013.01); *A61B 1/00006* (2013.01); *A61B 1/00188* (2013.01); *A61B 5/062* (2013.01); *G02B 23/2476* (2013.01); *H02K 41/0354* (2013.01); *A61B 2562/0223* (2013.01)

(58) Field of Classification Search
CPC ............ G02B 23/2438; G02B 23/2407; G02B 23/2423; G02B 23/2446; G02B 23/2476; G02B 23/2484; A61B 1/00059; A61B 1/00006; A61B 1/0002; A61B 1/00188;
(Continued)

(56) References Cited

U.S. PATENT DOCUMENTS 9,742,257 B2   8/2017 Shimoyama
9,769,384 B2   9/2017 Nishihara
(Continued)

FOREIGN PATENT DOCUMENTS

JP   2001174714 A   6/2001
JP   2009047951 A   3/2009
(Continued)

OTHER PUBLICATIONS

U.S. Appl. No. 16/688,652; First Named Inventor: Masanori Shimoyama; Title: "Endoscope System, Processor and Endoscope"; filed Nov. 19, 2019.
(Continued)

*Primary Examiner* — Ryan N Henderson
*Assistant Examiner* — Pamela F Wu
(74) *Attorney, Agent, or Firm* — Holtz, Holtz & Volek PC

(57) ABSTRACT

An endoscope system includes an endoscope in which an actuator moves a movable lens and a position sensor outputs a position detection signal, and a processor including a driver circuit configured to drive the actuator and a driving control circuit configured to subject a deviation of the position detection signal to first correction based on individual processor correction data stored in a processor memory and controls the driver circuit based on a target position and the position detection signal subjected to the first correction.

15 Claims, 5 Drawing Sheets

(51) Int. Cl.
*H02K 41/035* (2006.01)
*A61B 5/06* (2006.01)

(58) Field of Classification Search
CPC ..... A61B 1/00163; A61B 1/0019; A61B 1/04; A61B 1/05; A61B 1/045
USPC .......................................... 359/697; 600/163
See application file for complete search history.

(56) References Cited

U.S. PATENT DOCUMENTS

| | | | |
|---|---|---|---|
| 10,165,184 B2 | 12/2018 | Nishihara | |
| 10,379,373 B2 | 8/2019 | Nishihara | |
| 2011/0069164 A1 | 3/2011 | Ozawa et al. | |
| 2012/0050577 A1* | 3/2012 | Hongu | G02B 7/282 348/240.1 |
| 2012/0147341 A1* | 6/2012 | Tsukagoshi | H04N 9/317 353/121 |
| 2013/0041220 A1 | 2/2013 | Kutsuma | |
| 2016/0037079 A1 | 2/2016 | Gocho et al. | |
| 2016/0234427 A1* | 8/2016 | Yoshino | A61B 1/00009 |
| 2019/0053693 A1* | 2/2019 | Koiso | A61B 1/00013 |

FOREIGN PATENT DOCUMENTS

| | | |
|---|---|---|
| JP | 2009142586 A | 7/2009 |
| JP | 2011087910 A | 5/2011 |
| JP | 2013128663 A | 7/2013 |
| WO | 2012017735 A1 | 2/2012 |
| WO | 2015015877 A1 | 2/2015 |

OTHER PUBLICATIONS

U.S. Appl. No. 16/780,774 First Named Inventor: Masanori Shimoyama; Title: "Endoscope System, Processor, Calibration Apparatus, and Endoscope"; filed Feb. 3, 2020.
Japanese Office Action dated Sep. 27, 2022 (and English translation thereof) issued in counterpart JP Application No. 2018-227499.

* cited by examiner

FIG. 4

| ITEM | SECTION | SYMBOL | UNIT |
|---|---|---|---|
| LENS POSITION | ENDOSCOPE | x | [mm] |
| APPLIED MAGNETIC FIELD TO HALL ELEMENT | ENDOSCOPE | y0 | [mT] |
| OUTPUT VOLTAGE FROM HALL ELEMENT | ENDOSCOPE | y1 | [mV] |
| OUTPUT VOLTAGE FROM DIFFERENTIAL AMPLIFIER CIRCUIT | ENDOSCOPE | y2 | [mV] |
| OUTPUT OF ADC | PROCESSOR | y3 | [LSB] |
| OUTPUT OF FIRST CORRECTION UNIT | PROCESSOR | y4 | [LSB] |
| OUTPUT OF SECOND CORRECTION UNIT | PROCESSOR | y5 | [LSB] |

FIG. 5

| ITEM | SECTION | SYMBOL | UNIT | REMARK |
|---|---|---|---|---|
| DETECTION GAIN | ENDOSCOPE | a0 | [mT/mm] | CORRECTION BY SECOND CORRECTION UNIT |
| APPLIED MAGNETIC FIELD OFFSET | ENDOSCOPE | b0 | [mT] | CORRECTION BY SECOND CORRECTION UNIT DESIGNED CENTRAL VALUE IS "0" |
| HALL ELEMENT DRIVING CURRENT | PROCESSOR | a1 | [mA] | CORRECTION BY FIRST CORRECTION UNIT |
| HALL OUTPUT SENSITIVITY | ENDOSCOPE | a2 | [mV/mT/mA] | CORRECTION BY SECOND CORRECTION UNIT |
| HALL IMBALANCE VOLTAGE | ENDOSCOPE | b1 | [mV] | CORRECTION BY SECOND CORRECTION UNIT DESIGNED CENTRAL VALUE IS "0" |
| GAIN OF DIFFERENTIAL AMPLIFIER CIRCUIT | ENDOSCOPE | a3 | [-] | CORRECTION BY SECOND CORRECTION UNIT |
| IMBALANCE VOLTAGE OF DIFFERENTIAL AMPLIFIER CIRCUIT | ENDOSCOPE | b2 | [mV] | CORRECTION BY SECOND CORRECTION UNIT DESIGNED CENTRAL VALUE IS "0" |
| REFERENCE VOLTAGE OF DIFFERENTIAL AMPLIFIER CIRCUIT | PROCESSOR | b3 | [mV] | CORRECTION BY FIRST CORRECTION UNIT |
| GAIN OF ADC | PROCESSOR | a4 | [LSB/mV] | CORRECTION BY FIRST CORRECTION UNIT |
| OFFSET OF ADC | PROCESSOR | b4 | [LSB] | CORRECTION BY FIRST CORRECTION UNIT DESIGNED CENTRAL VALUE IS "0" |

ENDOSCOPE SYSTEM, PROCESSOR, AND ENDOSCOPE

CROSS REFERENCE TO RELATED APPLICATION

This application claims benefit of Japanese Application No. 2018-227499 filed in Japan on Dec. 4, 2018, the entire contents of which are incorporated herein by this reference.

BACKGROUND OF THE INVENTION

1. Field of the Invention

The present invention relates to an endoscope system in which an endoscope and a processor are connected to each other, a processor configured to control the endoscope, and the endoscope connected to the processor.

2. Description of the Related Art

An endoscope system includes an endoscope configured to observe a subject and a processor configured to control the endoscope, for example. In the endoscope system, a configuration for enabling an image forming state (e.g., a focus position and a zoom position) of an objective optical system configured to observe the subject to be adjusted has been proposed.

Examples of a technique associated with focus adjustment control of the endoscope include an endoscope system described in Japanese Patent Application Laid-Open Publication No. 2013-128663, for example. The endoscope system described in the publication includes an actuator including a shape memory element and configured to drive a moving member for moving an objective optical system, an actuator driving unit configured to drive the actuator, a resistance value detection unit configured to detect a resistance value of the shape memory element to detect a position of the moving member, an instruction input unit configured to receive an instruction to operate the objective optical system, a control unit configured to output a driving signal to the actuator driving unit based on the instruction inputted to the instruction input unit and a position of the moving member corresponding to the resistance value detected by the resistance value detection unit, and a storage unit connected to the control unit. As described in the publication, the control unit outputs to the actuator driving unit a driving signal for supplying to the actuator a current that monotonously increases at a predetermined rate from a predetermined start current value to a predetermined maximum current value when an instruction to perform calibration has been issued while storing in the storage unit the resistance value, which is equal to or more than a predetermined threshold, the value being obtained by secondarily differentiating a resistance value of the shape memory element detected by the resistance value detection unit and taking an absolute value of the differentiated value as the resistance value. Such a configuration causes the objective optical system to be moved to a far point focus position and a near point focus position, for example.

To accurately perform focus adjustment, a position of a lens (a focus lens, etc.) configured to move within the objective optical systems needs to be accurately detected.

As an example of a technique for detecting a lens position, Japanese Patent Application Laid-Open Publication 2009-47951 describes a lens position detection apparatus including an image pickup lens, a correction lens provided within the image pickup lens and movable with respect to an optical axis, a hall element held integrally with the correction lens, a driving coil configured to drive the correction lens, a magnet held relative to the driving coil, a current supply circuit configured to supply a current to the hall element, a first differential amplifier configured to control a power supply voltage of the hall element such that one of outputs of the hall element is the same as a reference voltage, a voltage amplifier circuit configured to amplify the outputs of the hall element, and a voltage correction circuit configured to provide an offset to an input voltage of the voltage amplifier circuit.

SUMMARY OF THE INVENTION

An endoscope system according to an aspect of the present invention includes an endoscope and a processor to which the endoscope is connected, in which the endoscope includes an objective optical system including a movable optical element and configured to form an optical image of a subject, an actuator configured to move the optical element, and a position sensor configured to output a position detection signal corresponding to a position of the optical element, and the processor includes a driver circuit configured to drive the actuator, a processor memory circuit configured to store individual processor correction data for correcting a deviation of the position detection signal caused by an individual variation of the processor, and a controller configured to subject the deviation of the position detection signal to first correction based on the individual processor correction data and control the driver circuit based on a target position of the optical element and the position detection signal subjected to the first correction such that a position of the optical element coincides with the target position.

A processor according to another aspect of the present invention, to which an endoscope configured to move an optical element included in an objective optical system by an actuator and output a position detection signal corresponding to a position of the optical element by a position sensor is connected, configured to control the endoscope, the processor including a driver circuit configured to drive the actuator, a processor memory circuit configured to store individual processor correction data for correcting a deviation of the position detection signal caused by an individual variation of the processor, and a controller configured to subject the deviation of the position detection signal to first correction based on the individual processor correction data and control the driver circuit based on a target position of the optical element and the position detection signal subjected to the first correction such that a position of the optical element coincides with the target position.

An endoscope according to still another aspect of the present invention is connected to a processor, the endoscope including an objective optical system including a movable optical element and configured to form an optical image of a subject, an actuator configured to move the optical element, and a position sensor configured to output a position detection signal corresponding to a position of the optical element, and an endoscope memory circuit storing individual endoscope correction data for correcting a deviation of the position detection signal caused by an individual variation of the endoscope.

BRIEF DESCRIPTION OF THE DRAWINGS

FIG. 4 is a table illustrating a classification of signals and the like that carry position information on an information transmission path in the first embodiment;

FIG. 5 is a table illustrating parameters when position information changes on the information transmission path in the first embodiment.

DETAILED DESCRIPTION OF THE PREFERRED EMBODIMENT

An embodiment of the present invention will be described below with reference to the drawings.

First Embodiment

Figure 1:
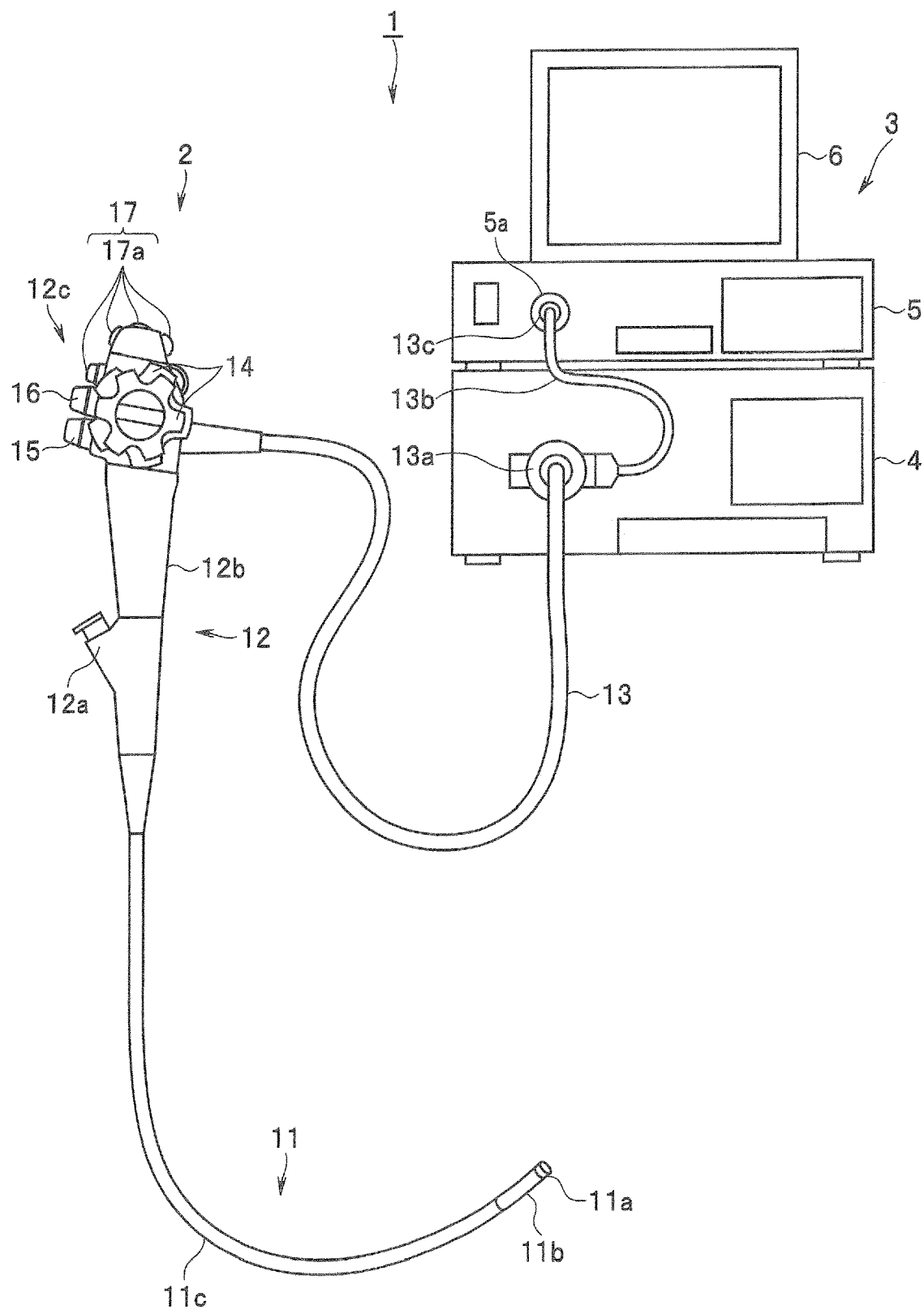
FIG. 1 is a diagram illustrating a configuration of an endoscope system in which an endoscope and a processor are detachably connected to each other in a first embodiment of the present invention.

FIGS. 1 to 6 illustrate a first embodiment of the present invention, where FIG. 1 is a diagram illustrating a configuration of an endoscope system 1 in which an endoscope 2 and a processor 3 are detachably connected to each other.

The endoscope system 1 as an image pickup apparatus according to the present embodiment is configured as an electronic endoscope system that picks up an optical image of a subject and outputs an image pickup signal, for example. The endoscope system 1 may be for any one of uses such as a medical use, an industrial use, and an academic use.

The endoscope system 1 includes an endoscope 2 and a processor 3 configured separately from the endoscope 2. The processor 3 includes a light source apparatus 4 configured to emit illumination light, a video processor 5 configured to process the image pickup signal from the endoscope 2, and a monitor 6 configured to display an endoscope image based on a video signal to be outputted from the video processor 5. Note that the monitor 6 needs not necessarily be included in the processor 3, but a separate external monitor may be used by being connected to the processor 3. The light source apparatus 4 may be configured integrally with the video processor 5.

The endoscope 2 includes an elongated insertion section 11 configured to be inserted into a subject, an operation section 12 provided on a distal end side of the insertion section 11, and a universal code 13 extending from a side portion, for example, of the operation section 12, and is configured as an electronic endoscope, as described below. However, the endoscope 2 is not limited to the electronic endoscope, but may be an optical endoscope if configured such that an actuator 23 (see FIG. 2) drives an objective optical system 21 (see FIG. 2), as described below.

The insertion section 11 includes a distal end section 11a, a bending section 11b, and a flexible tube section 11c in an order from its distal end side to the proximal end side. Although a case where the endoscope 2 is a flexible endoscope is taken as an example, the endoscope 2 may be a rigid endoscope.

An objective optical system 21 and an image pickup device 22 (see FIG. 2), an actuator 23 and a magnet 24 (see FIG. 2), a position sensor 25 (see, e.g., FIGS. 2 and 3), and the like are disposed within the distal end section 11a.

The operation section 12 includes a forceps port 12a, a grip unit 12b, and a user operation unit 12c.

The forceps port 12a is an opening portion on a proximal end side of a forceps channel provided within the insertion section 11. On the other hand, an opening portion on a distal end side of the forceps channel is arranged in the distal end section 11a. When a treatment instrument such as forceps is inserted from the forceps port 12a to protrude from the distal end section 11a, various types of treatment for a subject can be performed using the treatment instrument.

The grip unit 12b is a site configured to be grasped by a hand of an operator who operates the endoscope 2.

The user operation unit 12c is a site configured for the operator to perform various types of operations for the endoscope system 1 including the endoscope 2.

The user operation unit 12c includes two bending operation sections 14, an air/water feeding button 15, a suction button 16, and a switch section 17.

One of the two bending operation sections 14 is for subjecting the bending section 11b to a bending operation in an up-and-down direction, and the other bending operation section 14 is for subjecting the bending section 11b to a bending operation in a right-to-left direction. When the up-and-down bending and the right-to-left bending are combined with each other, the bending section 11b can be subjected to the bending operation in a desired direction.

The air/water feeding button 15 is an operation button configured to feed air/water toward the distal end section 11a via the above-described forceps channel, for example.

The suction button 16 is an operation button for performing suction from a side of the distal end section 11a via the above-described forceps channel, for example.

The switch section 17 is configured to include a plurality of switches 17a, and an operation associated with image pickup is mainly performed. For example, the certain switch 17a functions as a release button configured to pick up a still image, the other switch 17a functions as a freeze button configured to keep a video image during observation still by the monitor 6, and the still other switch 17a functions as a focus button configured to adjust a focus position of the objective optical system 21 (or which may be a zoom button configured to adjust a zoom position).

The universal code 13 contains a light guide bundle and a signal line. The light guide bundle is for transmitting the illumination light generated by the light source apparatus 4 to irradiate the illumination light onto the subject from an illumination window in the distal end section 11a. A signal line is used to transmit various types of signals associated with image pickup of the image pickup device 22, various types of signals associated with driving and position detection of the actuator 23, and endoscope information, for example.

A scope connector 13a configured to be detachably connected to the light source apparatus 4 is provided at a proximal end of the universal code 13. When the scope connector 13a is connected to the light source apparatus 4, the universal code 13 enters a state where the illumination light can be supplied to a proximal end of the light guide bundle.

A scope cable 13b containing the above-described signal line extends from a side portion, for example, of the scope connector 13a. An electrical connector 13c configured to be detachably connected to the video processor 5 is provided at a proximal end of the scope cable 13b. When the electrical connector 13c is connected to a connector receiver 5a in the video processor 5, an electrical circuit in the endoscope 2 and an electrical circuit in the video processor 5 are connected to each other via a signal line. Note that the scope cable 13b may be detachably attached to the scope connector 13a, or may be configured integrally with the universal code 13 and the scope cable 13b.

The video processor 5 supplies power to the endoscope 2, to control an electrical configuration of the endoscope 2. The video processor 5 processes an image pickup signal obtained from the image pickup device 22 in the endoscope 2, to generate a video signal.

The monitor 6 is configured as a color monitor, for example, and is connected to the video processor 5. The monitor 6 displays an endoscope image when receiving the video signal processed by the video processor 5. Further, various types of information about the endoscope system 1, for example, can also be displayed on the monitor 6.

Figure 2:
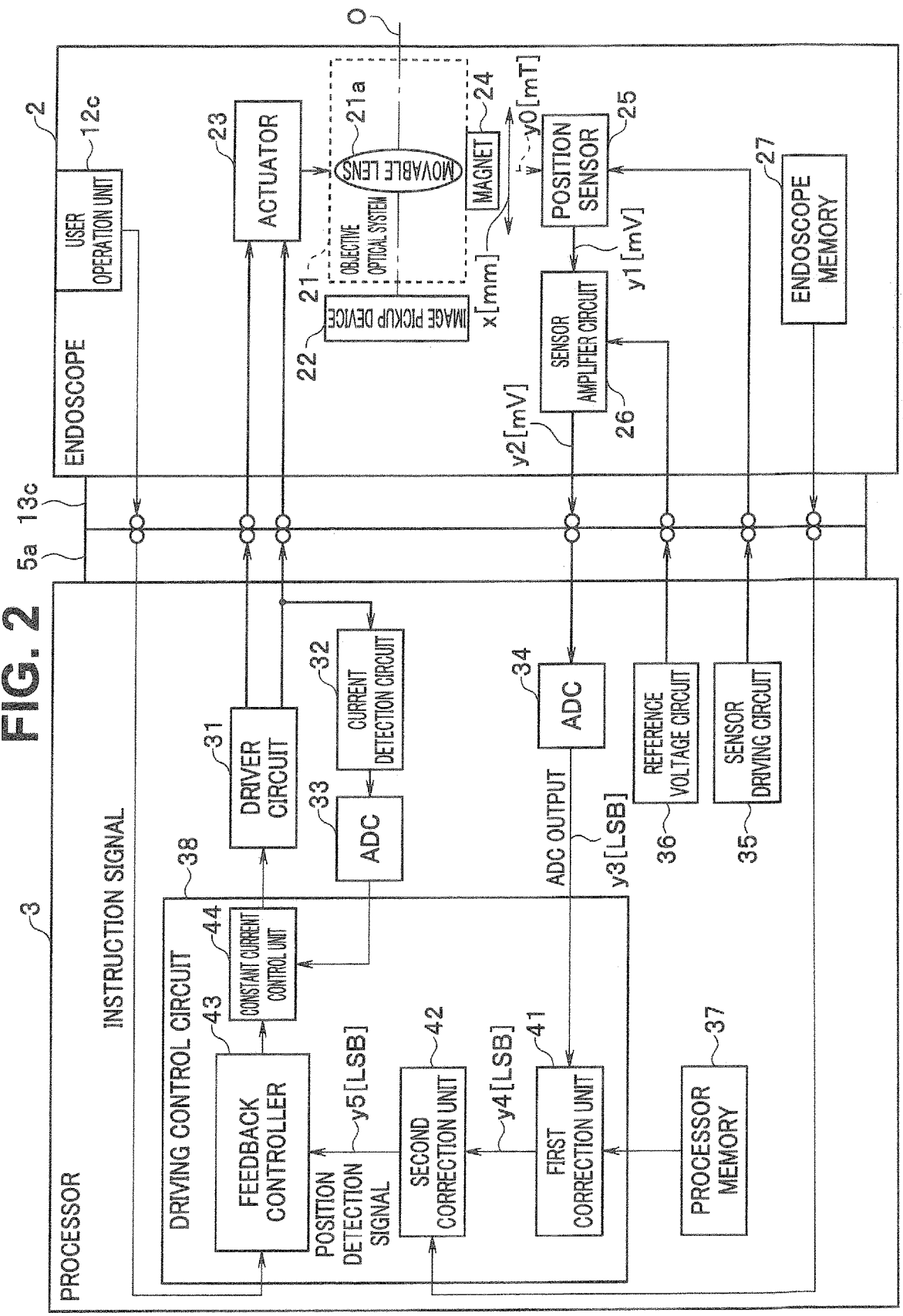
FIG. 2 is a diagram illustrating a principal part of an electrical and optical configuration of the endoscope and the processor associated with driving of an objective optical system in the first embodiment.

Then, FIG. 2 is a diagram illustrating a principal part of an electrical and optical configuration of the endoscope 2 and the processor 3 associated with the driving of the objective optical system 21. Note that in FIG. 2, a thin line arrow indicates a flow of a digital signal, and a normal-thickness arrow indicates a flow of an analog signal (a mere example representing the distinction between the digital signal and the analog signal is illustrated in FIG. 2).

The endoscope 2 includes the objective optical system 21, the image pickup device 22, the actuator 23, the magnet 24, the position sensor 25, and the user operation unit 12c, as described above, while further including a sensor amplifier circuit 26 and an endoscope memory 27.

The objective optical system 21 forms an optical image of the subject (a subject image) on an image pickup plane of the image pickup device 22. The objective optical system 21 includes a movable lens 21a, and the movable lens 21a is an optical element configured to be movable along an optical axis O of the objective optical system 21. When the movable lens 21a moves along the optical axis O, an image forming state of the objective optical system 21 is adjusted, and a focus position (or which may be a zoom position), for example, is changed. Therefore, the movable lens 21a functions as a focus lens (or a zoom lens), for example. Note that although the movable lens 21a is taken as an example of a movable optical element, the movable optical element is not limited to the lens, but may be other optical elements such as an optical filter, an optical aperture, and a mirror.

The image pickup device 22 has a plurality of pixels arranged on the image pickup plane, and generates an image pickup signal composed of a plurality of pixel signals by photoelectrically converting a subject image formed by the objective optical system 21 using each of the pixels. Note that an image pickup system of the image pickup apparatus is configured to include the objective optical system 21 and the image pickup device 22.

The actuator 23 moves the movable lens 21a along the optical axis O, and is configured as a voice coil motor (VCM) configured to generate a driving force with an electromagnetic force, for example (note that the actuator 23 is not limited to the voice coil motor).

The magnet 24 is composed of a permanent magnet or the like, and is arranged to move integrally with the movable lens 21a along the optical axis O. A magnetic field to be generated by the magnet 24 is used for the position sensor 25 to detect a position of the movable lens 21a configured to move integrally with the magnet 24. If the voice coil motor, for example, is used as the actuator 23, the magnet 24 can serve as a part of the voice coil motor (the configuration may be adopted from the viewpoint of realizing miniaturization of the distal end section 11a).

More specifically, the magnet 24 is fixed to a movable section such as a movable frame configured to hold the movable lens 21a, and a coil of the actuator 23 is attached to a fixing section such as a fixing frame configured to hold the movable frame movably along the optical axis O, for example. When a current is applied to a coil within the magnetic field to be generated by the magnet 24, a lorentz force is generated in the coil, and the movable section moves along the optical axis O by a reaction to the lorentz force because the fixing frame is fixed.

Note that a moving magnet type voice coil motor is adopted because the actuator 23 can be more easily miniaturized in a configuration in which a current is applied toward the fixing section than in a configuration in which a current is applied toward the movable section (a flexible printed circuit board, for example, needs to be used to apply a current toward the movable section, a position of which moves). Therefore, the moving coil type voice coil motor is not inhibited from being adopted.

The position sensor 25 is a position sensor arranged by being fixed to a side of the fixing section to oppose the magnet 24 and configured to detect a position along the optical axis O of the movable lens 21a and output a position detection signal. Although examples of the position sensor 25 in the present embodiment include a magnetic sensor such as a hall element configured to output a position detection signal (hall detection signal) corresponding to a magnetic flux density of the magnetic field to be generated by the magnet 24, the present invention is not limited to the hall element.

The sensor amplifier circuit 26 amplifies an analog position detection signal outputted from the position sensor 25. Examples of the sensor amplifier circuit 26 in the present embodiment include a differential amplifier circuit configured to amplify a hall voltage to be generated in response to a magnetic field density to be applied to the hall element within the magnetic field. However, the present invention is not limited to this.

Note that a specific configuration example of the position sensor 25 and the sensor amplifier circuit 26 will be described below with reference to FIG. 3.

The endoscope memory 27 is a nonvolatile memory circuit (endoscope memory circuit) configured to store individual endoscope correction data. A deviation of the position detection signal may occur on a side of the endoscope 2 or may occur on a side of the processor 3. The endoscope memory 27 stores individual endoscope correction data for correcting the deviation of the position detection signal occurring on the side of the endoscope 2.

The deviation of the position detection signal not only differs depending on a model of the endoscope 2 but also differs for each of individual endoscopes 2 of the same model, as represented by a data name "individual endoscope correction data". The individual endoscope correction data is data for appropriately correcting the deviation of the position detection signal caused by an individual variation of the endoscope 2 (a variation in mounting position of the magnet 24 on the movable lens 21a, a variation in mounting position of the position sensor 25 on the magnet 24, a variation in magnetization of the magnet 24, a variation in electrical characteristic of the position sensor 25, a variation in electrical characteristic of the sensor amplifier circuit 26, etc. in the configuration according to the present embodiment).

The endoscope memory 27 further stores model information (a model number, etc.) and a manufacturing number of the endoscope 2, various types of other information associated with the endoscope 2, and the like.

The user operation unit 12c includes the switches 17a configured to adjust the image forming state (the focus position, the zoom position, or the like) of the objective optical system 21, as described above. In other words, when a user operates the user operation unit 12c, an instruction signal representing a target position of the movable lens 21a is transmitted toward the processor 3 from the user operation unit 12c. As an example, the user operation unit 12c sets which of a far point focus position and a near point focus position is the target position of the movable lens 21a (note that a two-point focus of a far point and a near point is not a limitation but the focus position (or the zoom position) may be consecutively changed).

Note that although manual focusing by setting from the user operation unit 12c has been described, the present invention is not limited to this. Autofocus based on the image pickup signal obtained from the image pickup device 22, for example, may be performed.

As described above, the endoscope 2 is detachably attached to the processor 3 by detachably connecting the scope connector 13a to the light source apparatus 4 and detachably connecting the electrical connector 13c to the connector receiver 5a in the video processor 5.

The following are examples of a signal to be transmitted and received via the electrical connector 13c and the connector receiver 5a by the endoscope 2 and the processor 3.

The endoscope 2 transmits to the processor 3 the instruction signal from the user operation unit 12c, the position detection signal from the sensor amplifier circuit 26, and the data in the endoscope memory 27. The endoscope 2 receives from the processor 3 a driving signal to the actuator 23, a power supply signal and a reference voltage signal to the sensor amplifier circuit 26, a hall element current signal to the position sensor 25, and a ground signal (GND) as a reference (also see FIG. 3 described below).

The processor 3 controls the endoscope system 1 to emit the illumination light by the light source apparatus 4 and acquire the image pickup signal from the endoscope 2. The video processor 5 processes the image pickup signal to generate a video signal, outputs the video signal to the monitor 6, and displays an endoscope image or the like on the monitor 6. Since a known technique can be appropriately used for a configuration and a function associated with illumination and video signal processing related to the processor 3, detailed description is omitted.

The processor 3 includes a driver circuit 31, a current detection circuit 32, an ADC 33, an ADC 34, a sensor driving circuit 35, a reference voltage circuit 36, a processor memory 37, and a driving control circuit 38, respectively, as components associated with the driving of the objective optical system 21.

The driver circuit 31 outputs a driving signal to the actuator 23 and drives the actuator 23 based on control by the driving control circuit 38. More specifically, the driver circuit 31 applies a driving signal having a predetermined current value to the coil of the actuator 23 so that the movable section including the movable lens 21a and the magnet 24 is moved with an electromagnetic force.

The current detection circuit 32 detects the current value of the driving signal to be fed to the actuator 23 from the driver circuit 31, and outputs an analog current detection signal.

The ADC 33 is an analog-to-digital converter (A/D converter) configured to convert the analog current detection signal outputted from the current detection circuit 32 into a digital current detection signal.

The ADC 34 is an analog-to-digital converter (A/D converter) configured to convert the analog position detection signal outputted from the position sensor 25 and amplified by the sensor amplifier circuit 26 into a digital position detection signal.

The sensor driving circuit 35 is a constant current circuit configured to supply a hall element current as a current (constant current) having a constant current value to the position sensor 25 configured as a hall element, for example.

The reference voltage circuit 36 feeds a signal of an offset voltage as a reference voltage to the sensor amplifier circuit 26 configured as a differential amplifier circuit, for example.

The processor memory 37 is a nonvolatile memory circuit (processor memory circuit) storing individual processor correction data. The above-described individual endoscope correction data is data for appropriately correcting a deviation of the position detection signal occurring due to the individual variation of the endoscope 2, while the individual processor correction data is data for appropriately correcting a deviation of the position detection signal occurring due to an individual variation of the processor 3 (a variation in electrical characteristic of the reference voltage circuit 36, a variation in electrical characteristic of the sensor driving circuit 35, a variation in electrical characteristic of the ADC 34, etc.).

The processor memory 37 stores as a database information about the actuator 23, the position sensor 25, the sensor amplifier circuit 26, and the like previously found depending on model information and a manufacturing number of the endoscope 2.

Further, the processor memory 37 further stores various types of information associated with the processor 3 such as model information (a model number, etc.) and a manufacturing number of the processor 3, a processing program to be executed in the processor 3, various types of parameters to be used in the processor 3, and a setting value set for the endoscope system 1 by the user.

The driving control circuit 38 is configured to include an arithmetic processing circuit such as a CPU, and functions as each processing unit. The driving control circuit 38 is a controller (a control circuit) configured to control the driver circuit 31 such that a position of the movable lens 21a represented by the position detection signal matches the target position represented by the instruction signal from the user operation unit 12c.

More specifically, the driving control circuit 38 includes a first correction unit 41 and a second correction unit 42 as a correction unit, a feedback controller 43, and a constant current control unit 44.

The first correction unit 41 acquires the individual processor correction data from the processor memory 37, and subjects the digital position detection signal to be outputted from the ADC 34 to a variation caused by the individual processor 3, as described above, based on the acquired individual processor correction data.

The second correction unit 42 is arranged in a stage succeeding the first correction unit 41, for example, and acquires the individual endoscope correction data from the endoscope memory 27 and subjects the position detection signal corrected by the first correction unit 41 to a variation caused by the individual endoscope 2, as described above, based on the acquired individual endoscope correction data.

The feedback controller 43 issues, based on a difference value between a current position of the movable lens 21a represented by the position detection signal outputted from the second correction unit 42 (therefore a position detection signal corrected by the first correction unit 41 and the second correction unit 42) and the target position of the movable lens 21a represented by the instruction signal from the user operation unit 12c, an instruction about such a current value that the difference value becomes zero (that is, the position of the movable lens 21a coincides with the target position) to the constant current control unit 44.

The constant current control unit 44 controls, based on a current value represented by the current detection signal detected by the current detection circuit 32 and digitized by the ADC 33, the driver circuit 31 such that a current having the current value designated by the feedback controller 43 is outputted. As a result, the driver circuit 31 supplies the current having the designated current value to the actuator 23.

Thus, the feedback controller 43 and the constant current control unit 44 that constitute the controller (control circuit) perform feedback control such that the movable lens 21a reaches the target position.

Note that although the constant current control unit 44 controls the current to be supplied to the actuator 23 based on a result of the current detection by the current detection circuit 32 and the ADC 33 in the present embodiment, the present invention is not limited to this. For example, the present invention may have a configuration in which current detection is not performed.

For example, the present invention may have a configuration using the driver circuit 31 configured to apply a current that has been subjected to voltage control such as PWM (pulse width modulation) to the actuator 23, a resistance value of which has been previously known. In this case, in the configuration illustrated in FIG. 2, the current detection circuit 32, the ADC 33, and the constant current control unit 44 may be deleted, and a voltage control unit configured to control a voltage of a signal to be fed to the actuator 23 from the driver circuit 31 based on an output of the feedback controller 43 may be provided in the driving control circuit 38.

Further, the signal to be fed to the actuator 23 from the driver circuit 31 may be a signal that has been subjected to both current control and voltage control.

Figure 3:
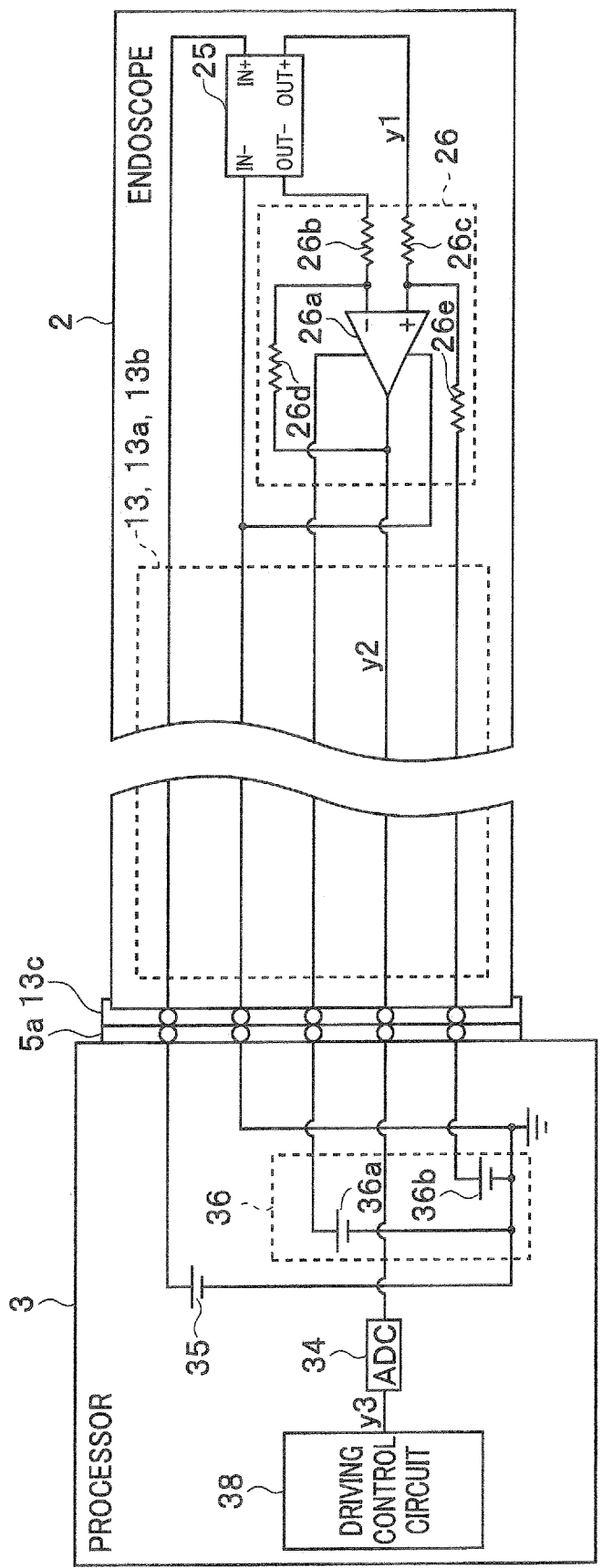
FIG. 3 is a diagram illustrating a configuration example of a position detection circuit configured to detect a position of a movable lens in the first embodiment.

Then, FIG. 3 is a diagram illustrating a configuration example of a position detection circuit configured to detect a position of the movable lens 21a.

As described above, the position sensor 25 is configured as a hall element, for example, and the sensor amplifier circuit 26 is configured as a differential amplifier circuit, for example. FIG. 3 specifically illustrates a circuit in such a configuration example.

The hall element is an element configured to output a detection signal corresponding to a magnitude of a magnetic flux density. In other words, when a magnetic field is applied in a direction perpendicular to a current direction to a hall element current (constant current) applied to the hall element, carriers (electrons, holes, etc.) receive a lorentz force in a direction (i×B direction) perpendicular to both a current direction (i direction) and a magnetic field direction (B direction). As a result, a difference occurs between respective distribution densities of carriers on both end surfaces in the i×B direction of the hall element. When a signal corresponding to the hall voltage is detected, the magnitude of the magnetic flux density received by the hall element can be measured.

Therefore, when the position sensor 25 configured as the hall element measures the magnetic flux density to be generated by the magnet 24 configured to move integrally with the movable lens 21a, a position of the magnet 24 and thus a position of the movable lens 21a can be measured. From such a reason, a signal corresponding to the hall voltage to be outputted from the position sensor 25 is referred to as a position detection signal.

The sensor driving circuit 35 in the processor 3 applies the above-described hall element current between an IN+ terminal and an IN− terminal of the position sensor 25. An OUT+ terminal and an OUT− terminal are respectively provided on both the end surfaces in the i×B direction of the above-described hall element.

The sensor amplifier circuit 26 is configured as a differential amplifier circuit including a differential amplifier 26a composed of an OP amplifier or the like and resistors 26a, 26b, 26c, 26d, and 26e, for example.

The OUT+ terminal of the position sensor 25 is connected to a positive terminal of the differential amplifier 26a via the resistor 26c, and the OUT− terminal of the position sensor 25 is connected to a negative terminal of the differential amplifier 26a via the resistor 26b.

The positive terminal of the differential amplifier 26a is connected to a differential amplification reference voltage power supply 36b in the reference voltage circuit 36 via the resistor 26e. The negative terminal of the differential amplifier 26a is connected to an output terminal of the differential amplifier 26a via the resistor 26d. Further, a driving current is supplied from a power supply 36a in the reference voltage circuit 36 to the differential amplifier 26a. The output terminal of the differential amplifier 26a is connected to the ADC 34 in the processor 3. The ADC 34 is connected to the first correction unit 41 in the driving control circuit 38, as described above.

Then, a change of position information of the movable lens 21a on an information transmission path occurring until the position information is inputted to the feedback controller 43 in the driving control circuit 38 will be described with reference to FIGS. 2 to 5. FIG. 4 is a table illustrating a classification of signals and the like that carry position information on the information transmission path, and FIG. 5 is a table illustrating parameters when the position information changes on the information transmitted path.

As illustrated in FIGS. 4 and 2, the signals and the like that carry the position information on the information transmission path are represented using symbols, as described below.

For each of the units within the endoscope 2, a position of the movable lens 21a, a magnetic flux density to be applied to the position sensor 25 by the magnet 24, a voltage value (hall voltage value) of an output from the position sensor 25, and a voltage value of an output from the sensor amplifier circuit 26 are respectively represented by x (mm), y0 (mT), y1 (mV), and y2 (mV).

Further, for each of the units within the processor 3, a signal value to be outputted by the ADC 34, a signal value to be outputted by the first correction unit 41, and a signal value to be outputted by the second correction unit 42 are respectively represented by y3 (LSB), y4 (LSB), and y5 (LSB).

At this time, within the endoscope 2, information about the position x of the movable lens 21a to be borne by the magnetic flux density y0 deviates from an actual position x due to a variation in magnetization of the magnet 24, a variation in mounting position of the magnet 24 on the movable lens 21a, and the like. Similarly, information about the position x of the movable lens 21*a* to be borne by the voltage value y1 and information about the position x of the movable lens 21*a* to be borne by the voltage value y2 also deviate due to a change in waveform of an analog signal, for example.

Assuming that the position of the movable lens 21*a* to be borne by the voltage value y2 from the endoscope 2 has changed to x', x' can be expressed as given by the following Equation 1, using a function C1 representing a change of position information within the endoscope 2:

$$x'=C1(x) \quad \text{[Equation 1]}$$

Similarly, within the processor 3, information about the position x of the movable lens 21*a* to be borne by the signal value y3 also deviates due to a conversion error at the time of AD conversion, for example. When the ADC 34 receives the voltage value y2 that bears information about the position x', if the position of the movable lens 21*a* to be borne by the signal value y3 has changed to x", x" can be expressed as given by the following Equation 2 using a function C2 representing a change of position information within the processor 3:

$$x''=C2(x') \quad \text{[Equation 2]}$$

Therefore, information about the position x" to be received by the driving control circuit 38 is expressed as follows using a composite function C2·C1 of the function C1 and the function C2:

$$x''=C2(C1(x))=C2 \cdot C1(x)$$

Generally, the function C1 and the function C2 are non-commutative:

$$C2 \cdot C1(x) \neq C1 \cdot C2(x)$$

Accordingly, to obtain information about the position x, from which an influence of the deviation has been removed, from the information about the position x", an arithmetic operation as expressed by the following Equation 3 is performed for the position x" using an inverse function C1^−1 of the function C1 and an inverse function C2^−1 of the function C2:

$$x=C1\text{^}{-}1\{C2\text{^}{-}1(x'')\} \quad \text{[Equation 3]}$$

In other words, to correct the deviation of position information that has occurred on the information transmission path, a procedure of first correcting a deviation that has occurred within the processor 3 and then correcting a deviation that has occurred within the endoscope 2 is used.

Accordingly, the signal value y3 to be outputted by the ADC 34 is first corrected by the first correction unit 41 using the individual processor correction data, and is then corrected by the second correction unit 42 using the individual endoscope correction data.

Note that if the function C1 and the function C2 are commutative, and the following equation holds (or if processing may become complicated), respective processing orders of the first correction unit 41 and the second correction unit 42 may be replaced:

$$C2 \cdot C1(x)=C1 \cdot C2(x)$$

The first correction unit 41 and the second correction unit 42 may be combined together as one correction unit, and deviation correction, as expressed by the Equation 3, may be performed by the one correction unit.

In the configuration as illustrated in FIG. 2, the first correction unit 41 subjects the signal value y3 to be outputted by the ADC 34 to first correction f1 (correction for finding the signal value y4 that bears the information about the position x' from the signal value y3 that bears the information about the position x" described above), to calculate the signal value y4 as expressed by the following Equation 4:

$$y4=f1(y3) \quad \text{[Equation 4]}$$

Although f1 corresponds to the above-described inverse function C2^−1, C2^−1 is for converting the position x" into the position x', while f1 is for converting the signal value y3 into the signal value y4. Therefore, f1 and C2^−1 generally differ from each other.

The second correction unit 42 subjects the signal value y4 to second correction f2 (correction for finding the signal value y5 that bears the information about the position x from the signal value y4 that bears the information about the position x' described above), to calculate the signal value y5 as expressed by the following Equation 5:

$$y5=f2(y4) \quad \text{[Equation 5]}$$

Similarly, although f2 corresponds to the above-described inverse function C1^−1, C1^−1 is for converting the position x' into the position x, while f2 is for converting the signal value y4 into the signal value y5. Therefore, f2 and C1^−1 generally differ from each other.

Although the first correction f1 and the second correction f2, described above, respectively become general functions corresponding to actual machines of the endoscope 2 and the processor 3, a case where relatively highly accurate correction can be performed by a linear equation particularly is considered also in consideration of linearity of the position x and the magnetic flux density y0, for example.

At this time, when a zero order correction coefficient corresponding to the signal value y3 is represented by C0p and a first order correction coefficient corresponding to the signal value y3 is represented by C1p in the processor 3, the Equation 4 is expressed as given by the following Equation 6:

$$y4=C1p \times y3+C0p \quad \text{[Equation 6]}$$

When a zero order correction coefficient corresponding to the signal value y4 is represented by C0s and a first order correction coefficient corresponding to the signal value y4 is represented by C1s in the endoscope 2, the Equation 5 is expressed as given by the following Equation 7:

$$y5=C1s \times y4+C0s \quad \text{[Equation 7]}$$

Thus, the endoscope memory 27 stores C0s and C1s, for example, as the individual endoscope correction data, and the processor memory 37 stores C0p and C1p, for example, as the individual processor correction data. The storage in the endoscope memory 27 is performed at the time of shipment inspection from a factory of the endoscope 2, for example, and the storage in the processor memory 37 is performed at the time of shipment inspection from a factory of the processor 3, for example.

Note that although the correction has been performed using the linear equation, the correction may be performed using a quadratic equation or may be corrected using more complicated correction equations other than the quadratic equation if a higher accuracy is required.

Although the correction coefficients C0s and C1s as the individual endoscope correction data and the correction coefficients C0p and C1p as the individual processor correction data may be respectively found by testing the actual machines, the correction coefficients C0p and C1p, for example, can also be derived by giving parameters based on a configuration of each of the circuits.

Respective specific examples of the correction coefficients C0p and C1p when the change of the position information in each of the sections on the information transmission path can be described with high accuracy using the linear equation will be described.

As described above, the magnet 24 is configured to move integrally with the movable lens 21a. Therefore, when the movable lens 21a moves so that the position x changes, the magnet 24 also moves so that the position of the magnet 24 changes, and the magnetic flux density y0 to be incident on the position sensor 25 from the magnet 24 changes.

When a ratio of change (also referred to as a detection gain) of the magnetic flux density y0 (mT) to the position x (mm) of the movable lens 21a is represented by a0 (mT/mm), and an applied magnetic field offset is represented by b0 (mT), a relationship between the position x and the magnetic flux density y0 in first order approximation is described as expressed by the following Equation 8:

$$y0 = a0 \times x + b0 \qquad \text{[Equation 8]}$$

Then, when a hall element driving current value of the position sensor 25 is represented by a1 (mA), a hall output sensitivity (hall element output sensitivity) is represented by a2 (mV/mT/mA), and a hall imbalance voltage value (hall element imbalance voltage value) is represented by b1 (mV), the voltage value y1 (mV) of the signal to be outputted by the position sensor 25 that has received the magnetic flux density y0 (mT) is described as expressed by the following Equation 9:

$$y1 = a1 \times a2 \times y0 + b1 \qquad \text{[Equation 9]}$$

Then, when a gain of the sensor amplifier circuit 26 is represented by a3 (a dimensionless quantity), an imbalance voltage value is represented by b2 (mV), and a reference voltage value is represented by b3 (mV), the voltage value y2 (mV) of the signal to be outputted from the sensor amplifier circuit 26 that has received the voltage value y1 (mV) from the position sensor 25 is described as expressed by the following Equation 10:

$$y2 = a3 \times y1 + b2 + b3 \qquad \text{[Equation 10]}$$

Further, when a gain of the ADC 34 is represented by a4 (LSB/mV), and an offset of the ADC 34 is represented by b4 (LSB), the digital signal value y3 (LSB) to be outputted by the ADC 34 that has received the signal having the voltage value y2 (mV) from the sensor amplifier circuit 26 is described as expressed by the following Equation 11:

$$y3 = a4 \times y2 + b4 \qquad \text{[Equation 11]}$$

If the Equations 8 to 11 are used, the signal value y3 to be outputted by the ADC 34 is described as expressed by the following Equation 12 as a linear function using coefficients A and B of the position x of the movable lens 21a:

$$y3 = A \times x + B \qquad \text{[Equation 12]}$$
$$A = a4 \times a3 \times a2 \times a1 \times a0$$
$$B = a4 \times a3 \times a2 \times a1 \times b0 + a4 \times a3 \times b1 +$$
$$a4 \times (b2 + b3) + b4 = a4 \times b3$$

Note that the last equation for the coefficient B uses a fact that an applied magnetic field offset b0, a hall imbalance voltage value b1, an imbalance voltage value b2 of the sensor amplifier circuit 26, and an offset b4 of the ADC 34 can be designed such that a designed central value becomes "0" (see FIG. 5).

Although the Equation 12 indicates a relational equation in the designed central value (target value), each of values a1, b3, a4, and b4 has a variation error for each of individual processors 3 in an actual product.

When the value including the variation error for the processor 3 is written as a value followed by a prime ('), a relationship between a signal value y3' of the output of the ADC 34 for the individual processor 3 having values a1', b3', a4', and b4' and the position x of the movable lens 21a is described as expressed by the following Equation 13:

$$y3' = A' \times x + B'$$
$$A' = a4' \times a3 \times a2 \times a1' \times a0$$
$$B' = a4' \times b3' + b4' \qquad \text{[Equation 13]}$$

If the first correction unit 41 performs correction such that the signal value y3' expressed by the Equation 13 matches the signal value y3 based on the designed central value expressed by the Equation 12, an individual variation of the processor 3 can be canceled.

Therefore, if the signal value y3 based on the designed central value is substituted into y4 in the Equation 6 as a correction equation by the first correction unit 41, and the actual signal value y3' is substituted into y3 in the Equation 6, the following Equation 14 is obtained.

$$y3 = C1p \times y3' + C0p \qquad \text{[Equation 14]}$$

If the Equation 12 and the Equation 13 are substituted into the Equation 14, a first order correction coefficient C1p and a zero order correction coefficient C0p are found as expressed by the following Equation 15:

$$C1p = A/A' = a1 \times a4(a1' \times a4') \qquad \text{[Equation 15]}$$
$$C0p = B - (A/A') \times B' =$$
$$a4 \times b3 - a1 \times a4/(a1' \times a4') \times (a4' \times b3' + b4')$$

Therefore, the correction coefficients C0p and C1p as the individual processor correction data to be stored in the processor memory 37 are calculated based on the values a1, b3, and a4 based on the designed central value (target value) in the processor 3 and the values a1', b3', a4', and b4' for each of individual processors 3. The values a1', b3', a4', and b4' for the individual processor 3 are acquired by performing actual measurement, for example, with the endoscope 2 as a reference connected to the processor 3, for example, in a process for adjusting the processor 3.

The values include the hall element driving current values a1 and a1' to be outputted from the sensor driving circuit 35, the reference voltage values b3 and b3' of the signal to be outputted from the reference voltage circuit 36, the gains a4 and a4' of the ADC 34, and the offset b4' of the ADC 34, which are all values on the side of the processor 3. Therefore, in calculating the correction coefficients C0p and C1p as the individual processor correction data, the values on the side of the endoscope 2 (the values a0, b0, a2, b1, a3, and b2 indicated in a section "endoscope" illustrated in FIG. 5) need not be used. Thus, the correction coefficients C0p and C1p can be stored in the processor memory 37 as information specific to the processor 3.

However, for example, the hall element driving current value a1 (the target value) to be outputted from the sensor driving circuit 35 may differ depending on a model number or the like of the position sensor 25 loaded into the endoscope 2, the reference voltage value b3 (the target value) to be outputted from the reference voltage circuit 36 may differ depending on a circuit configuration of the sensor amplifier circuit 26 loaded into the endoscope 2, and the gain a4 (the target value) and the offset b4 (the target value) to be set in the ADC 34 may differ depending on the output signal from the endoscope 2. A configuration of a circuit unit loaded into the endoscope 2 not only differs depending on the model number of the endoscope 2 but also a lot of the product, for example.

Thus, the individual processor correction data (the correction coefficients C0p and C1p) corresponding to the model number and the manufacturing number of the endoscope 2, for example, are stored as a database in the processor memory 37. When the processor 3 and the endoscope 2 are connected to each other, the individual processor correction data (the correction coefficients C0p and C1p) corresponding to the model number and the manufacturing number of the endoscope 2 are acquired from the processor memory 37 and are used for the correction by the first correction unit 41.

Note that the database of the individual processor correction data can be appropriately updated to a newest database when the processor 3 is maintained, for example, and can also correspond to an endoscope 2 having a newest model number and a newest manufacturing number.

Figure 6:
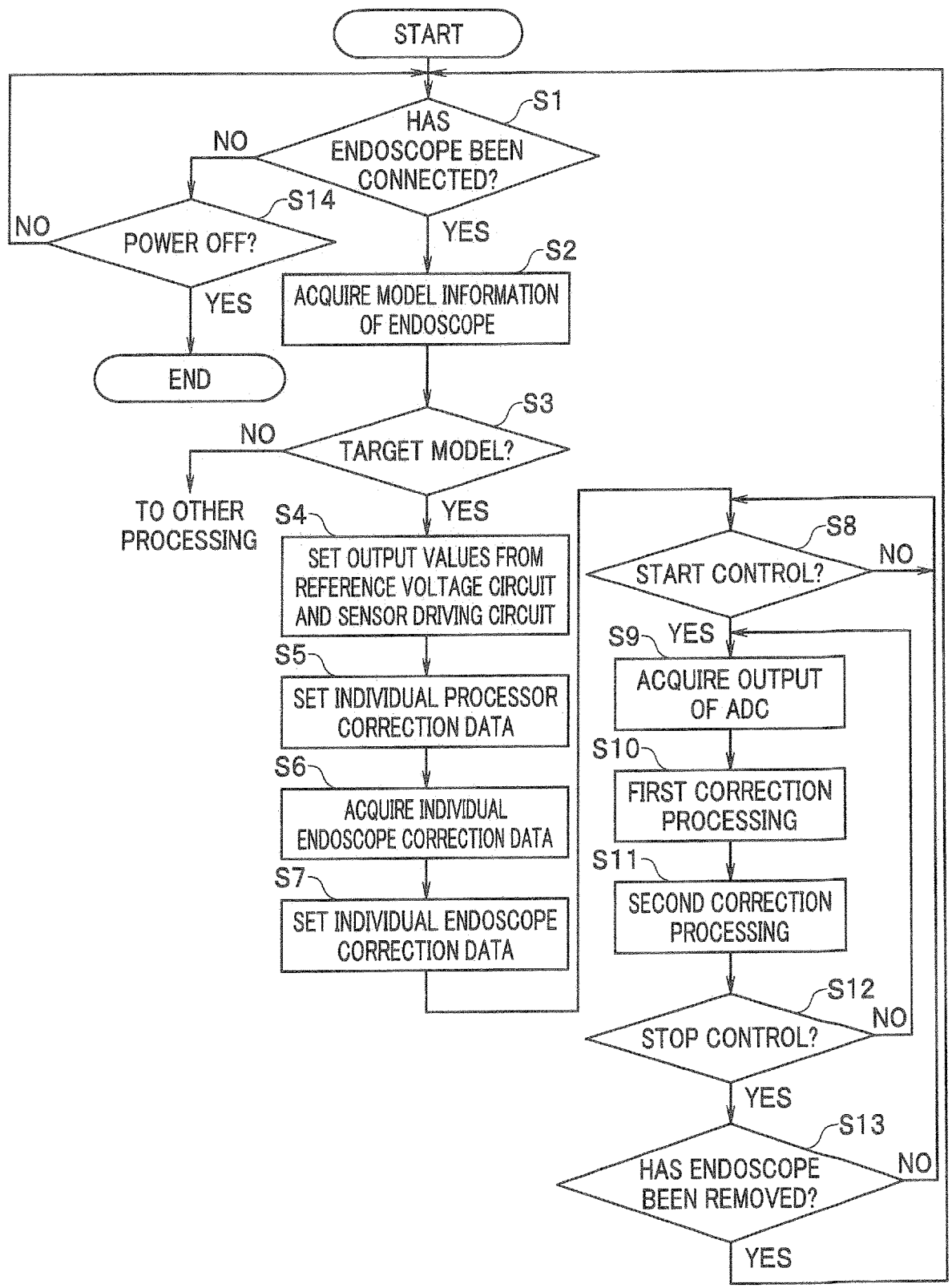
FIG. 6 is a flowchart illustrating processing for correcting a position detection signal to be performed by the processor in the first embodiment.

Then, FIG. 6 is a flowchart illustrating processing for correcting the position detection signal performed by the processor 3.

When power to the processor 3 is turned on, the processing is started. First, the driving control circuit 38 judges whether or not the endoscope 2 has been connected to the processor 3 (step S1).

If it is judged that the endoscope 2 has been connected to the processor 3, the driving control circuit 38 acquires model information such as a model number and a manufacturing number of the endoscope 2 from the endoscope memory 27 (step S2).

The driving control circuit 38 judges based on the acquired model information whether or not a model of the endoscope 2 connected to the processor 3 is a target model to correct the position detection signal (step S3). The judgment is performed based on whether or not the acquired model information matches model information stored in the database of the processor memory 37, for example.

If it is judged that the model of the endoscope 2 is not the target model, the processing proceeds to other processing such as processing for performing endoscope observation without correcting the position detection signal but using the position detection signal as it is.

If it is judged that the model of the endoscope 2 is the target model in step S3, the processor 3 sets the hall element driving current value a1 to be outputted from the sensor driving circuit 35 and the reference voltage value b3 to be outputted from the reference voltage circuit 36 based on the acquired model information while also setting the gain a4 of the ADC 34, for example, as needed (step S4).

Each of the values to be set in step S4 may be read from the endoscope memory 27 in the endoscope 2 in step S2. If each of the values is previously stored in the database of the processor memory 37, the value may be used.

Further, the driving control circuit 38 reads out the individual processor correction data from the processor memory 37, and sets the individual processor correction data in the first correction unit 41 (step S5).

The driving control circuit 38 acquires the individual endoscope correction data from the endoscope memory 27 (step S6), and sets the individual endoscope correction data in the second correction unit 42 (step S7).

Then, the endoscope observation is started, and the feedback controller 43 judges whether or not the instruction signal for changing the focus position (or the zoom position) of the objective optical system 21 has been inputted from the user operation unit 12c (step S8).

If it is judged that the instruction signal has not been inputted, the driving control circuit 38 waits until the instruction signal is inputted.

Thus, if it is judged that the instruction signal has been inputted in step S8, the feedback controller 43 subjects the constant current control unit 44 to feedback control based on a target position represented by the instruction signal and a current position represented by the position detection signal. As a result, the constant current control unit 44 drives the actuator 23 via the driver circuit 31.

The driving control circuit 38 acquires the signal value y3 of the position detection signal to be generated by the position sensor 25 and inputted via the sensor amplifier circuit 26 and the ADC 34 (step S9).

The first correction unit 41 corrects the position detection signal based on the Equation 6 using the correction coefficients C0p and C1p read out from the processor memory 37 (step S10). As a result, an individual variation of the processor 3 is corrected so that highly accurate position detection can be performed. At this time, the position detection signal can be corrected at high speed using a low-load arithmetic operation because the Equation 6 is a linear equation.

Then, the second correction unit 42 further corrects the signal value y4 of the position detection signal corrected by the first correction unit 41 based on the Equation 7 using the correction coefficients C0s and C1s read out from the endoscope memory 27 (step S11). As a result, an individual variation of the endoscope 2 is corrected so that more highly accurate position detection can be performed. At this time, the position detection signal can be corrected at high speed using a low-load arithmetic operation because the Equation 7 is a linear equation. Thus, the correction processing in steps S10 and S11 is performed at high speed so that real time performance of the position detection is also enhanced.

The feedback controller 43 acquires the corrected position detection signal from the second correction unit 42, and judges whether or not control of the position of the movable lens 21a represented by the position detection signal is stopped based on whether or not the position of the movable lens 21a has reached the target position inputted from the user operation unit 12c (step S12). Note that the judgment whether or not the control of the position is stopped may be performed based on whether or not a stopping operation has been performed from the user operation unit 12c.

If it is judged that the control is not stopped, the processing returns to step S9. In step S9, the above-described processing is repeatedly performed. The control of the position of the movable lens 21a performed while confirming the position detection signal by the feedback controller 43 is performed as feedback control to repeatedly perform a loop operation for each control sampling time period, as illustrated in steps S9 to S12.

If it is judged that the control is stopped in step S12, the driving control circuit 38 judges whether or not the endoscope 2 has been removed from the processor 3 (step S13).

If it is judged that the endoscope 2 has not been removed from the processor 3, the processing proceeds to step S8, described above, for the driving control circuit 38 to wait until a new instruction signal is inputted from the user operation unit 12c.

On the other hand, if it is judged that the endoscope 2 has been removed from the processor 3 in step S13, the processing proceeds to step S1, described above, for the driving control circuit 38 to wait until the same endoscope 2 is connected again to the processor 3 or the other endoscope 2 is newly connected to the processor 3.

If it is judged that the endoscope 2 has not been connected to the processor 3 in step S1, the driving control circuit 38 judges whether or not an operation for tuning off the power to the processor 3 has been performed (step S14).

If it is judged that the power off operation has not been performed, the processing proceeds to step S1, described above.

If it is judged that the power off operation has been performed in step S14, the processing ends.

According to the first embodiment, the processor memory 37 stores the individual processing correction data, and the deviation of the position detection signal is corrected based on the individual processor correction data. Therefore, the position of the movable lens 21a can be accurately detected without depending on the individual variation of the processor 3. As a result, the movable lens 21a can be accurately moved to the target position.

Thus, a dedicated electrical circuit including a plurality of switches and a plurality of resistors configured to adjust the position detection signal is not required. Therefore, highly accurate position detection can be performed while suppressing an increase in cost and an increase in size of the apparatus.

The first correction unit 41 corrects the position detection signal received from the endoscope 2 by the linear equation using the zero order correction coefficient C0p and the first order correction coefficient C1p. Therefore, the real time performance of the position detection can be enhanced by reducing an arithmetic operation load and shortening an arithmetic operation time period.

Further, the zero order correction coefficient C0p and the first order correction coefficient C1p are calculated based on the Equation 15. Therefore, the individual processor correction data can be calculated as information about the processor 3 alone independent of the endoscope 2. Further, an arithmetic operation can be performed by addition, subtraction, multiplication, and division. Therefore, a position detection signal that is aligned with the designed central value (target value) of the processor 3 can be obtained by relatively simple calculation.

The endoscope memory 27 further stores the individual endoscope correction data, and the deviation of the position detection signal is corrected based on the individual endoscope correction data. Therefore, the position of the movable lens 21a can be more accurately detected without depending on the individual variation of the endoscope 2. As a result, the movable lens 21a can be accurately moved to the target position.

At this time, the processor memory 37 stores the individual processor correction data, and the endoscope memory 27 stores the individual endoscope correction data. Therefore, even if the endoscope 2 and the processor 3 are connected to each other in any combination of models and any combination of individuals, the position detection signal can be appropriately corrected to perform highly accurate position detection. Thus, the movable lens 21a can be more accurately moved to the target position.

In addition, the second correction unit 42 is arranged in a stage succeeding the first correction unit 41. Therefore, correction can be performed by following processes in which the position detection signal deviates in reverse so that processing can be performed without complicating a correction arithmetic operation.

The second correction unit 42 corrects the position detection signal received from the first correction unit 41 by the linear equation using the zero order correction coefficient C0s and the first order correction coefficient C1s. Therefore, even if the individual variation of the endoscope 2 is corrected, the real time performance of the position detection can also be enhanced by reducing an arithmetic operation load and shortening an arithmetic operation time period.

Further, the magnet 24 is arranged in the movable lens 21a, and the position sensor 25 including the hall element detects the position of the movable lens 21a. Therefore, the configuration for the position detection can be miniaturized, which is appropriate for the endoscope 2 required for miniaturization and reduction in diameter. At this time, the position sensor 25 is fixed to the side of the fixing section. Therefore, wiring to the position sensor 25 becomes easy.

The sensor driving circuit 35 is set as a constant current circuit. Therefore, when the position sensor 25 is driven, a current value does not change, and a plurality of correction coefficients C0p and C1p corresponding to the current value need not be stored. Therefore, a storage capacity of the processor memory 37 can be saved.

In addition, the sensor amplifier circuit 26 is set as a differential amplifier circuit. Therefore, the voltage of the signal to be outputted from the hall element can be effectively amplified. The position sensor 25 is arranged in the distal end section 11a in the endoscope 2. Therefore, the position detection signal to be outputted from the position sensor 25 is transmitted by a certain distance until it reaches the processor 3. However, an S/N ratio of the position detection signal to be transmitted to the processor 3 from the endoscope 2 can be enhanced so that accurate position detection can be performed because the position detection signal has been amplified by the differential amplifier circuit.

If the movable lens 21a is for adjusting the focus position or the zoom position of the objective optical system 21, movement to an accurate focus position or movement to an accurate zoom position can be performed.

Note that processing for each of the above-mentioned units may be performed by one or more processors each configured as hardware. For example, each of the units may be a processor configured as an electronic circuit, or may be a circuit unit in a processor composed of an integrated circuit such as an FPGA (field programmable gate array). Alternatively, when a processor composed of one or more CPUs reads and executes a processing program recorded on a recording medium, a function as each unit may be performed.

Although the endoscope system, the processor, and the endoscope have been mainly described above, the present invention may be an operation method for operating the endoscope system, the processor, and the endoscope in a manner described above, or may be a processing program for causing a computer to perform similar processing to the processing of the endoscope system, the processor, and the endoscope or a computer readable non-transitory recording medium configured to record the processing program, for example.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope system comprising an endoscope and a processor to which the endoscope is connected, wherein:
the endoscope comprises:
an objective optical system including a movable optical element and configured to form an optical image of a subject,
an actuator configured to move the optical element, and
a position sensor configured to output a position detection signal corresponding to a position of the optical element; and
the processor comprises:
a driver circuit configured to drive the actuator,
a processor memory circuit configured to store individual processor correction data for correcting a deviation of the position detection signal caused by an individual variation of the processor, and
a controller configured to: i) subject the deviation of the position detection signal to a first correction based on the individual processor correction data, and ii) control the driver circuit based on a target position of the optical element and the position detection signal subjected to the first correction, such that a position of the optical element coincides with the target position; and
wherein:
the first correction is correction by a linear formula using a zero order correction coefficient C0p and a first order correction coefficient C1p for the position detection signal received from the endoscope, and
the individual processor correction data includes the zero order correction coefficient C0p and the first order correction coefficient C1p.

2. The endoscope system according to claim 1, wherein:
the endoscope further comprises:
a sensor amplifier circuit configured to amplify the position detection signal outputted from the position sensor;
the position detection signal from the endoscope to the processor is an analog signal;
the processor further comprises:
an analog-to-digital converter configured to convert the analog position detection signal received from the endoscope into a digital position detection signal,
a sensor driving circuit configured to supply a current to the position sensor, and
a reference voltage circuit configured to feed a signal having a reference voltage value to the sensor amplifier circuit;
the first correction is correction for the digital position detection signal obtained by the conversion by the analog-to-digital converter, and
the zero order correction coefficient C0p and the first order correction coefficient C1p are respectively calculated as values expressed by following formulas based on a current value a1' of a current supplied by the sensor driving circuit, a target value a1 of the current value, the reference voltage value b3', a target value b3 of the reference voltage value, a gain a4' of the analog-to-digital converter, a target value a4 of the gain, and an offset b4' of the analog-to-digital converter:

$$C1p = a1 \times a4/(a1' \times a4')$$

$$C0p = a4 \times b3 - a1 \times a4/(a1' \times a4') \times (a4' \times b3' + b4').$$

3. The endoscope system according to claim 2, wherein:
the endoscope further comprises a magnet configured to move integrally with the optical element,
the position sensor includes a hall element fixed in the endoscope, and
a magnetic flux density applied to the hall element from the magnet changes depending on movement of the optical element and the magnet.

4. The endoscope system according to claim 3, wherein:
the sensor driving circuit is a constant current circuit configured to supply a current having a predetermined current value to the hall element.

5. The endoscope system according to claim 3, wherein:
the sensor amplifier circuit is a differential amplifier circuit configured to amplify a voltage occurring in the hall element depending on the applied magnetic flux density.

6. The endoscope system according to claim 1, wherein:
the endoscope further comprises an endoscope memory circuit configured to store individual endoscope correction data for correcting a deviation of the position detection signal caused by an individual variation of the endoscope, and
the controller:
further performs a second correction by acquiring the individual endoscope correction data and correcting the deviation of the position detection signal based on the individual endoscope correction data, and
controls the driver circuit based on the position detection signal subjected to the first correction and the second correction.

7. The endoscope system according to claim 6, wherein:
the controller performs the second correction in a stage succeeding the first correction.

8. The endoscope system according to claim 7, wherein:
the second correction is correction by a linear formula using a zero order correction coefficient C0s and a first order correction coefficient C1s for the position detection signal subjected to the first correction, and
the individual endoscope correction data includes the zero order correction coefficient C0s and the first order correction coefficient C1s.

9. The endoscope system according to claim 1, wherein:
the optical element is a movable lens configured to adjust a focus position and a zoom position of the objective optical system,
the actuator moves the movable lens in an optical axis direction of the objective optical system, and
the position sensor outputs the position detection signal corresponding to a position in the optical axis direction of the movable lens.

10. A processor for controlling an endoscope, wherein the endoscope is capable of moving an optical element included in an objective optical system by an actuator and outputting a position detection signal corresponding to a position of the optical element by a position sensor, the processor comprising:
a driver circuit configured to drive the actuator;
a processor memory circuit configured to store individual processor correction data for correcting a deviation of the position detection signal caused by an individual variation of the processor; and
a controller configured to: i) subject the deviation of the position detection signal to a first correction based on the individual processor correction data, and ii) control the driver circuit based on a target position of the optical element and the position detection signal subjected to the first correction, such that a position of the optical element coincides with the target position,
wherein:
the first correction is correction by a linear formula using a zero order correction coefficient C0p and a first order correction coefficient C1p for the position detection signal received from the endoscope, and
the individual processor correction data includes the zero order correction coefficient C0p and the first order correction coefficient C1p.

11. The processor according to claim 10,
wherein the position detection signal from the endoscope to the processor is an analog signal; and
wherein the processor further comprises:
an analog-to-digital converter configured to convert the analog position detection signal received from the endoscope into a digital position detection signal,
a sensor driving circuit configured to supply a current to the position sensor, and
a reference voltage circuit configured to feed a signal having a reference voltage value to the sensor amplifier circuit configured to amplify the position detection signal provided in the endoscope;
wherein the first correction is correction for the digital position detection signal obtained by the conversion by the analog-to-digital converter, and
wherein the zero order correction coefficient C0p and the first order correction coefficient C1p are respectively calculated as values expressed by following equations formulas based on a current value $a1'$ of a current supplied by the sensor driving circuit, a target value $a1$ of the current value, the reference voltage value $b3'$, a target value $b3$ of the reference voltage value, a gain $a4'$ of the analog-to-digital converter, a target value $a4$ of the gain, and an offset $b4'$ of the analog-to-digital converter:

$$C1p = a1 \times a4/(a1' \times a4')$$

$$C0p = a4 \times b3 - a1 \times a4/(a1' \times a4') \times (a4' \times b3' + b4').$$

12. The processor according to claim 11, wherein:
the controller:
further performs second correction by acquiring individual endoscope correction data for correcting a deviation of the position detection signal caused by an individual variation of the endoscope from an endoscope memory circuit in the endoscope, and correcting the deviation of the position detection signal based on the individual endoscope correction data, and
controls the driver circuit based on the position detection signal subjected to the first correction and the second correction.

13. The processor according to claim 12, wherein:
the controller performs the second correction in a stage succeeding the first correction.

14. The processor according to claim 12, wherein:
the second correction is correction by a linear formula using a zero order correction coefficient C0s and a first order correction coefficient C1s included in the individual endoscope correction data for the position detection signal subjected to the first correction.

15. An endoscope connected to a processor, the endoscope comprising:
an objective optical system including a movable optical element and configured to form an optical image of a subject;
an actuator configured to move the optical element; and
a position sensor configured to output a position detection signal corresponding to a position of the optical element; and
an endoscope memory circuit storing individual endoscope correction data for correcting a deviation of the position detection signal caused by an individual variation of the endoscope,
wherein the individual endoscope correction data includes a zero order correction coefficient C0s and a first order correction coefficient C1s for correcting the position detection signal by a linear formula.

* * * * *